United States Patent [19]

Lamb et al.

[11] Patent Number: 4,489,387
[45] Date of Patent: Dec. 18, 1984

[54] METHOD AND APPARATUS FOR COORDINATING MEDICAL PROCEDURES

[76] Inventors: David E. Lamb, 708 Nottingham Rd., Newark, Del. 19711; William B. Long, 2747 Second Ave., Apt. J., San Diego, Calif. 92103; William J. Sacco, 803 Jackson Blvd., Bel Air, Md. 21014

[21] Appl. No.: 294,671

[22] Filed: Aug. 20, 1981

[51] Int. Cl.³ .............................................. G06F 15/42
[52] U.S. Cl. ..................................... 364/514; 128/630
[58] Field of Search ................. 364/414, 415; 128/630

[56] References Cited

U.S. PATENT DOCUMENTS

| | | |
|---|---|---|
| 3,355,370 | 2/1971 | Worthington, Jr. et al. |
| 3,725,866 | 4/1973 | Oldfield, Jr. et al. |
| 3,794,982 | 2/1974 | McCormick et al. |
| 3,810,102 | 5/1974 | Parks et al. ........................ 364/200 |
| 3,872,448 | 3/1975 | Mitchell, Jr. ...................... 364/200 |
| 3,934,226 | 1/1976 | Stone et al. ....................... 364/200 |
| 4,130,881 | 12/1978 | Haessler et al. ................. 364/415 X |
| 4,150,284 | 4/1979 | Trenkler et al. ................. 364/415 X |
| 4,216,462 | 8/1980 | McGrath et al. .................... 364/415 |
| 4,270,547 | 6/1981 | Steffen et al. ..................... 364/415 |
| 4,290,114 | 9/1981 | Sinay ............................. 364/415 X |
| 4,356,475 | 10/1982 | Neumann et al. ............. 364/415 X |
| 4,370,983 | 2/1983 | Lichtenstein ..................... 128/630 |

OTHER PUBLICATIONS

Shock Trauma Manual–William Gill, William Broughton Long III, pp. 90, 116 and 194.

*Primary Examiner*—Edward J. Wise
*Attorney, Agent, or Firm*—William D. Hall

[57] ABSTRACT

This invention relates to methods and apparatus for medical decision making. In particular, this invention coordinates the actions of two or more medical teams who are working toward a common goal. The apparatus used to achieve this objective consists of a control unit especially adapted for instructing, through algorithms, two or more teams of personnel to make observations and measurements, to answer questions, and to perform procedures independently and frequently simultaneously in a coordinated manner to achieve a common goal. The control unit interfaces with each medical team through an information display screen and data entry panel (I/O station). Based on information provided by medical personnel via the data entry panel in response to questions displayed on the display screen and/or information directly transmitted to the computer system from apparatus which measures variables relevant to the medical condition of the patient, the medical teams are advised simultaneously or alternatively to perform diagnostic and therapeutic procedures according to a predetermined plan. A log may be printed of the questions asked, the answers given, the treatment given and the monetary charges.

29 Claims, 8 Drawing Figures

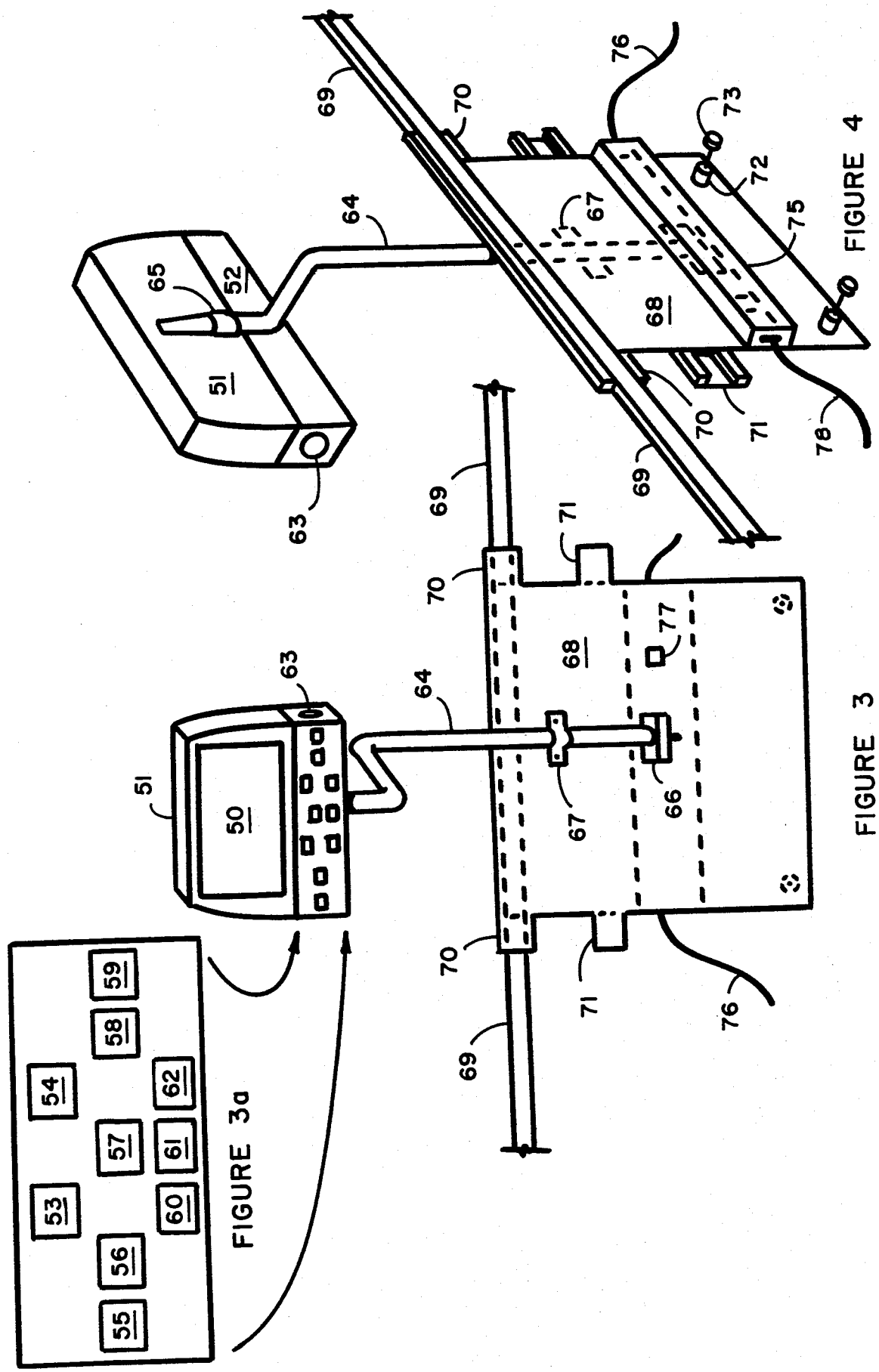

METHOD AND APPARATUS FOR COORDINATING MEDICAL PROCEDURES

This invention relates to methods and apparatus for medical decision making. In particular, this invention relates to medical methods and apparatus for the gathering of data concerning a specific patient and the direction of teams of medical personnel performing medical procedures on this patient in a coordinated manner.

BACKGROUND OF THE INVENTION

Medical intervention to increase the probability of patient survival or to reduce the time required for recuperation often requires performance of complex medical procedures. The procedures to be performed and the sequence in which they are performed is determined by medical personnel based on an assessment of the medical condition of the patient. When the patient's condition undergoes rapid change, as often occurs in critical cases, it is necessary to rapidly adapt medical procedures to the changing condition of the patient. Decisions must be made rapidly, and stress on the decision makers is often high. Such an environment is conducive to errors which can have serious or fatal results for the patient.

The probability of error can be reduced by defining medical procedures in terms of algorithms which specify the sequence of steps that must be performed to accomplish the procedures. More complex algorithms can be defined which are designed to aid medical personnel in determining the proper sequence in which medical procedures should be performed.

Through the use of medical algorithms, experts in various medical specialities can convey to practitioners the description of medical procedures in a clear and unambiguous manner and additionally can specify contingency actions to be taken conditional on the changing medical condition of a patient. Current practice consists of representing the algorithms graphically in the form of tree structures. These tree structures contain branch points which direct the practitioner to alternative sequences of steps conditional on the medical condition of the patient or on treatment previously administered to the patient. Binary tree structures are designed such that at each branch point there exist only two alternative paths that may be followed. The choice of which of the two paths is to be followed can be determined be asking the medical practitioner a question to which the response must be either "yes" or "no." Thus, although the tree structure is determined by the designer of the algorithm, the path that is taken by the practitioner in traversing the tree is determined primarily by the practitioner's answers to questions posed by the algorithm.

Medical algorithms in the form of tree structures have been published in books and manuals and are useful for training purposes. However, there is no system currently in use which is capable of providing ready access to these expert developed plans for a treating physician at a time of crisis. Further, there is no mechanized system in use which can lead two or more medical personnel simultaneously through an algorithm and coordinate their actions toward the common goal of providing optimal treatment for a patient in a time of crisis.

SUMMARY OF THE INVENTION

There are a number of types of medical problems that require the coordination of two or more groups of medical personnel who are treating a patient. One example is the case of a cardiac arrest. Another example is a patient with multiple blunt trauma injuries. Still another example is a soldier who has suffered several major injuries and has been brought to a military hospital.

In the example of the cardiac arrest, the patient may be on a bed in the emergency room. One group or team of medical personnel may be located on one side of the bed and a second team of medical personnel may be located on the other side of the bed.

This invention comprises in part, a first input/output (I/O) station located adjacent the first team and a second I/O station located adjacent the second team.

Each I/O station has a plurality of push buttons. Moreover, each I/O station has a display screen readily visible to the team of medical personnel adjacent that panel.

The I/O stations are connected to a computer which is controlled by a program which reads information from a database. The database is selected according to the patient's problem. If the patient has a cardiac arrest, the computer Data Base applicable to that medical problem is selected.

Pursuing the case of the cardiac arrest as an example, the program will first cause one of the I/O stations to ask a question which will be displayed on its display screen. Such a question could be, "Is the patient's systolic blood pressure below 80?" At the same time that the question is displayed, two of the push buttons, one marked "YES" and the other "NO," will be lit up on the I/O station. The physician adjacent the I/O station then presses the applicable button. At the same time that one physician is answering this question at one I/O station, another physician may be answering another question displayed at the I/O station adjacent to his position.

Based on the answer to these initial questions, the computer selects the next questions for the I/O station(s). Or, instead of a question, the computer may feed one or both of the I/O stations with instructions. The entire series of the operations of the two groups of medical personnel are coordinated by the computer in this manner. The computer communicates with the two I/O stations to receive information on the patient's condition. The computer, in turn, causes the I/O stations to ask further questions and/or give further instructions. This sequence continues until resuscitation of the patient is accomplished or until a decision is made to terminate the resuscitation effort.

Well constructed medical data bases designed to be used in conjunction with this invention can help two or multiple teams of physicians and nurses perform independently, but in a coordinated manner, complex diagnostic and therapeutic procedures on a critically ill patient and thereby reduce delay in effective diagnostic treatment and hence lower mortality and speed recovery.

The text of the relevant medical program is conveyed to the medical teams in the form of sequences of steps called frames. Generally, each frame provides a single question and/or instruction to a physician for each I/O station involved. Furthermore, the questions or instructions (as the case may be) provided to one I/O station are usually different than the one or ones provided to the other I/0 station(s). In order to advance the computer to the next frame, the physicians at each I/O station must respond to the questions and/or instructions. In the case of a question, a physician responds by pressing a button which conveys the answer to the question to the computer. For convenience and accuracy in answering questions, the two or more buttons which may be depressed to answer the question are illuminated. In the case of the I/O station giving an instruction for a given treatment to a physician, one or more buttons may be illuminated so that the physician may respond to the instruction. Pressing one of these buttons will indicate to the computer that the instruction was carried out. Pressing one or more other buttons may give other indications to the computer such as that the instruction could not be carried out.

Ordinarily, the first few frames comprise questions and the subsequent frames comprise questions and instructions.

Above all, however, the several frames supply the two or more I/O stations with different coordinated questions and/or instructions, so that the plural medical teams act in unison and perform their respective chores in the proper sequence. In other words, the system comprising this invention assumes at least part of the role of the chief physician in that it directs the acts of the two or more medical teams so that they work together, and never work at cross-purposes.

Other unique and optional features of the system include internal counters which count the cumulative dosage and number of times a drug is given and reminds the doctor that further administration of the drug will cause toxicity and recommends an alternative therapy. The program used may also instruct the respiratory therapist to change patterns of ventilation, the nurse to administer sodium bicarbonate, or one or both medical teams to redirect their attentions to check out the oxygen delivery system and the patient's pulmonary system, based on periodic blood gas analysis.

The computer may be connected to a printer which produces a printout of the events that occurred during the treatment of the patient. The charges for the various treatments and medicines administered are stored in a computer memory and are printed out when applicable and ultimately totalized.

In a more simplified form, this computer system with I/O stations could be used for critical situations outside of the hospital setting, for example, by paramedics either in their ambulance or at the side of a patient lying on the ground.

It is also possible that a computer system according to this invention could be used for the training of medical personnel who want to specialize in emergency medicine.

The system can be designed such that I/O stations communicate with the complementary medical personnel by audible signals in combination with the visual displays or even by audible signals alone.

IN THE DRAWINGS

FIG. 3 is a perspective view of the front of one embodiment of an input/output station according to this invention.

FIG. 3a is an enlarged view of the arrangement of the pushbuttons of the I/O station illustrated in FIG. 3.

FIG. 4 is a perspective view of the back of the input/output station illustrated in FIG. 3.

DETAILED DESCRIPTION OF THE DRAWINGS

Figure 1:
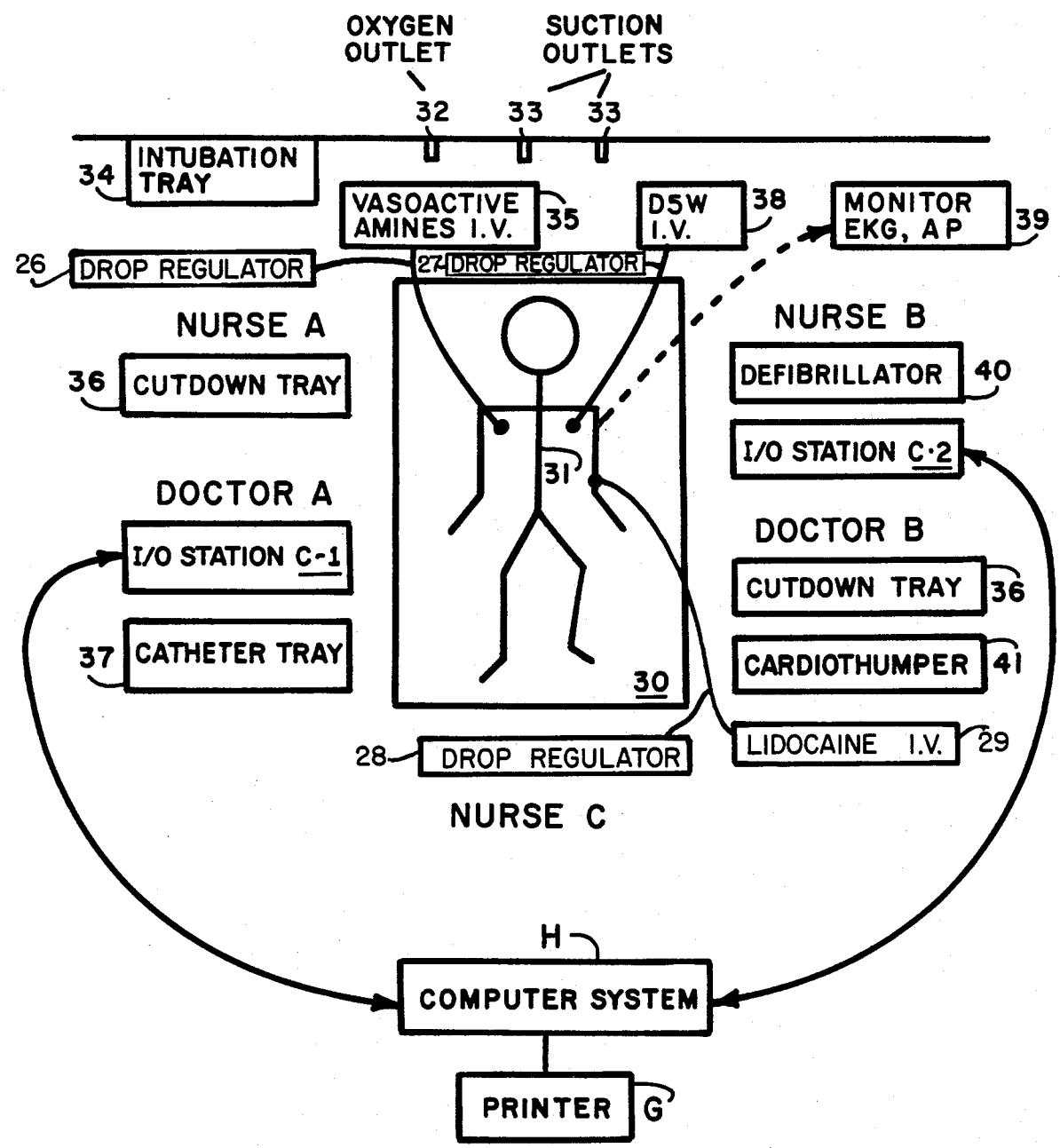
FIG. 1 is a schematic drawing illustrating the invention in one environment in which the invention can be employed.

Referring to the Figures, a computer system especially adapted for organizing medical teams and assisting the teams in patient diagnosis and in making therapeutic decisions concerning critically ill or injured patients is provided. The system is designed to function in an environment in which specific equipment is required and arranged around a patient's bed 30 (or a stretcher or an operating room table) where two or more medical teams (for example, Doctors A and B and Nurses A, B and C) will be treating patient 31 as shown in FIG. 1. The equipment shown in FIG. 1 is set up in particular to handle a patient in a cardiac arrest. The equipment used during medical procedures directed by this invention may vary depending on the patient's medical problems.

Two suction outlets 33 are located at the head of the bed and can either be portable suction units or connected to the hospital's suction system. Oxygen outlet 32, also located at the patient's head, must be connected to the hospital's oxygen delivery system. Oxygen outlet 32, which must be capable of delivering at least 40 liters of oxygen per minute, powers cardiothumper 41.

Arranged around the patient's bed 30 (or stretcher or operating table) are the following items (see FIG. 1):

a. Intubation tray 34 which should consist in part of an adult and pediatric laryngoscope having adjustable tongue blades and a light source. Also located on intubation tray 34 are variable sizes of endotracheal tubes, inflatable cuffs, and a flexible wire stylet.

b. Located on both sides of patient 31 are cutdown trays 36. Cutdown trays 36 are sterile cutdown trays that are standard hospital equipment consisting of a number of surgical instruments for exposing veins and arteries for the purpose of catherization.

c. A Foley catheter tray 37 is located near the foot of bed 30 and consists of the necessary equipment for catherizing a patient's urinary bladder.

d. On the patient's left side is located defibrillator 40 preferably of the square wave direct current type which is capable of delivering up to 400 Joules of energy to the patient. Defibrillator 40 should contain paddles for both internal and external cardiac application.

e. Cardiothumper 41 is located on the patient's bed 30 at the chest level and is arranged for compression of the lower half of the sternum of patient 31. Cardiothumper 41 is attached to oxygen outlet 32 and adjusted according to the directions given by Doctor A.

f. Vasoactive amines IV 35 are located on the patient's right shoulder and consist of an IV pole with three bags containing a mixture of sterile 5% dextrose and water. One bag should remain plain, the second bag should contain the drug Isoproterenol, and the third bag should contain Dopaminehydrochloride. Each bag shall be connected to a four-way stop cock by sterile IV tubing. The four-way stop cock will then be attached to a catheter inserted into a major vein in the patient's neck, right side of his neck, or right shoulder. The rate of infusion is controlled by a drop regulator 26.

g. Located near the patient's left shoulder is another IV pole, D5W IV 38, containing a bag containing a mixture of sterile 5% dextrose and water. D5W IV 38 is attached to a catheter in the patient's left side of his neck or his left shoulder by means of sterile IV tubing. The IV tubing shall contain a rubber connector for the purpose of giving drugs by Bolus injection. The rate of infusion is controlled by a drop regulator 27.

h. Located just off the patient's left shoulder is monitor EKG and AP 39 which is capable of recording on a screen an electrocardiogram tracing and the tracing for the arterial blood pressure. Monitor EKG and AP 39 shall be conntected to the patient via EKG leads and tubing joined in the arterial pressure transducer and a catheter inserted into an artery in one of the patient's extremities.

i. Located near the patient's left arm is another IV pole, lidocaine IV 29, on which hangs a bag containing a mixture of sterile 5% dextrose and water and the drug lidocaine. This solution is connected to IV tubing which is in turn attached to a drip regulator 28, which controls the rate of infusion. The sterile IV tubing in turn is connected to a catheter in a major vein in the patient's left arm.

Medical teams are arranged around the patient as follows: A respiratory therapist and/or an anaesthesiologist, not shown in FIG. 1, stand at the head of the patient's bed and are responsible for monitoring the patient's airway, intubating the patient, and ventilating the patient. Doctor A, the physician in charge and the medical team captain, stands to the patient's right and is responsible for the use of the cardiothumper 41, inserting the intravenous catheters on the patient's right side of the body, and interacting with I/O station C-1 (described in detail later). Doctor B stands on the left side of the patient (the patient's left) where he is responsible for inserting intravenous catheters in the patient's left side of the body, performing the arterial catherization, and directing the defibrillation of the patient. Doctor B interacts with I/O station C-2, which will be later discussed in detail. Nurse A assists Doctor A and may or may not interact with I/O station C-1 or another I/O station as may be applicable. Nurse B assists Doctor B and may or may not interact with I/O station C-2 or another I/O station as may be applicable. Nurse C stands at the foot of the bed and acts as a circulating nurse providing equipment and materials for both Doctor A and Doctor B and interacts with I/O station C-2 or another I/O station as may be applicable.

The I/O stations C-1 and C-2 are connected either by cable or telemetry to a computer system H consisting of components A, B, D, E, and F as outlined in FIG. 2 and as will be later discussed in detail.

Upon notification of a situation involving a patient from outside of the hospital such as an ambulance telemetry unit calling in and describing a critical situation, Doctor A would activate the computer system through I/O station C-1 and obtain, if possible, advance information about the patient from the ambulance personnel. Based on the nature of the patient's problem, Doctor A would then select the appropriate program dealing with the patient's condition. For example, if a patient had a cardiac arrest, Doctor A would select on computer system H the module for treating cardiac arrest.

Once the proper module is selected, the computer system H would begin by asking Doctor A questions concerning the physical features of the patient. Based on the information Doctor A is able to obtain from the ambulance personnel, Doctor A keys in the responses to the questions posed by computer system H, which in turn asks additional questions or instructs Doctor A and Doctor B through I/O stations C-1 and C-2 respectively to perform certain procedures. These instructions may include a list of procedures to be completed to prepare for the patient's arrival. The questions directed by computer system H to Doctor A via I/O station C-1 may consist of questions like, "Does the patient weight more than 200 pounds?" Doctor A then presses either the "YES" button or the "NO" button, which are on I/O station C-1, depending upon the information derived from the ambulance personnel. The keyed-in information regarding the patient's weight then enables computer system H to issue a set of instructions to Doctor A and Doctor B regarding the size of catheters to be inserted into the patient and the dosages of the drugs to be given to the patient. If the paramedics are unable to give this information or the information is not available, then the system and doctors have to wait until the patient arrives before these questions can be answered and the appropriate instructions given.

Upon arrival of the patient, the control Doctor A continues the interaction with computer system H via the I/O station C-1 by pushing the button labeled "NEXT." I/O station C-1 then issues a further set of instructions and/or questions. At some time during this process, the computer system H activates the I/O station C-2 and in turn issues instructions or asks questions different from the instructions and questions transmitted or being transmitted to I/O station C-1.

Thus, computer system H issues instructions or asks questions on one or more of the I/O stations based on the information keyed into the system through the input buttons of the I/O stations and/or information transmitted to computer system H directly from apparatus I which consists of devices such as EKG and AP monitors and/or other apparatus which measures patient variables or makes other analyses relevant to the medical condition of the patient. The information relayed to each I/O station may be different or similar to the information fed to other station(s) depending upon the decisions made and the information keyed in at each I/O station. The system coordinates the activities at the I/O stations and directs the medical teams in a manner such that the correct procedures are performed in the correct sequence.

Computer system H is connected to a printer G (more fully described later with reference to FIG. 2) which keeps a log of the decisions made and the procedures performed and does other things as required.

There are other medical conditions to which this system could apply besides cardiac arrest as described above. For example, a patient with multiple gunshot wounds or multiple traumatic injuries sustained in an automobile accident could be brought to a hospital where this system could be installed. The equipment required for treating these patients would essentially be the same as shown in FIG. 1, however, additional equipment could be added to either side of the patient as necessary. For example, a tray for performing a laparotomy or a thoracotomy could be a part of the equipment around Doctor A or Doctor B. For a trauma patient, instead of infusions of 5% dextrose and water, there may be liter bags of Ringer's lactate, blood transfusions apparatus, etc.

In the emergency department setting, the I/O stations C-1 and C-2 and other I/O stations would usually be arranged on walls of the hospital room set aside for the purpose of resuscitation of critically ill or injured patients. The I/O stations of this system could ordinarily be attached to railings that are attached to these walls.

In the context of the intensive care unit or a bed on the intensive care floors of a hospital, this method of displaying the I/O stations may not be applicable. Under these circumstances, the unit may be portable or the I/O stations could be attached to the computer system itself.

Figure 2:
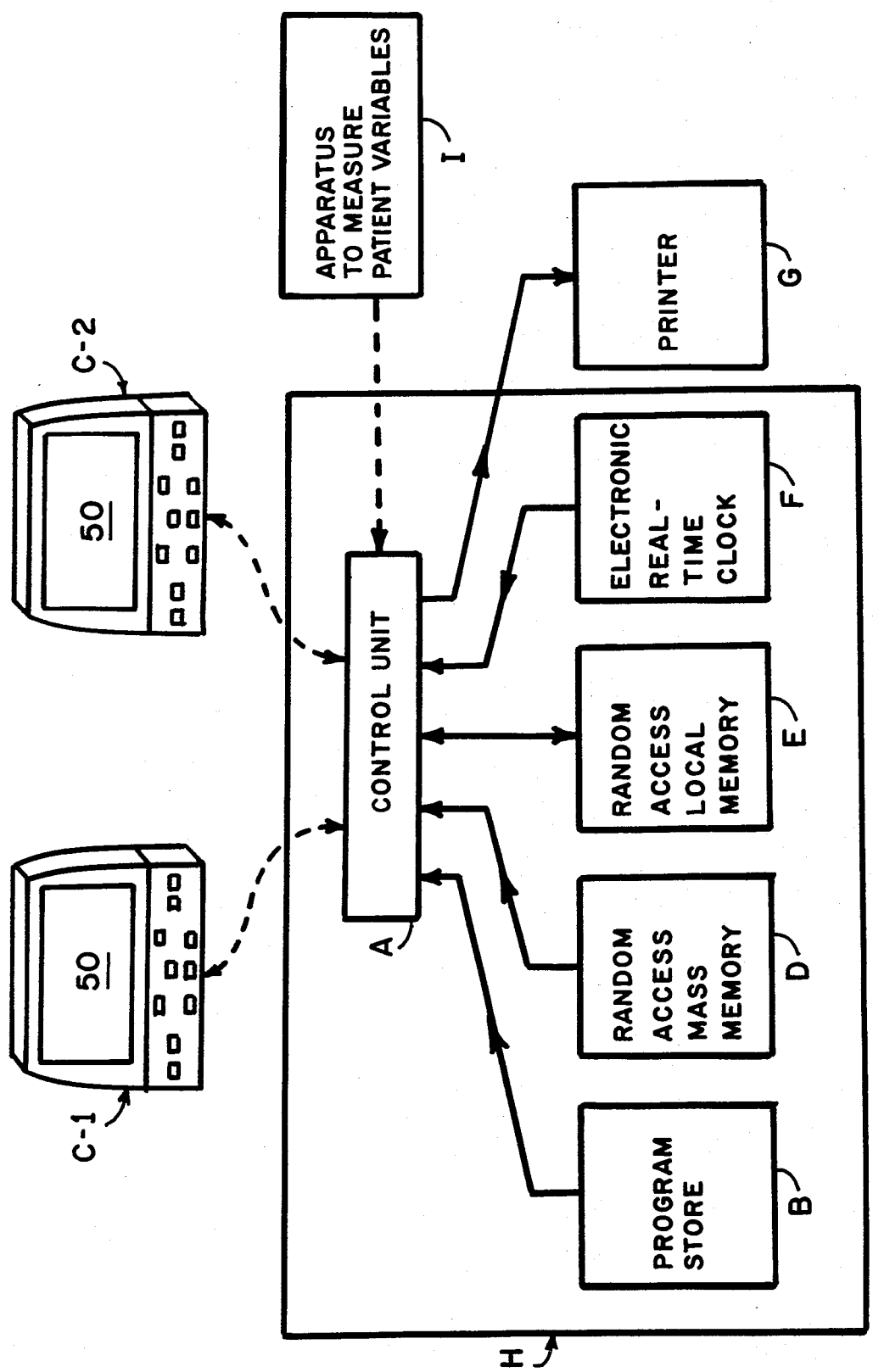
FIG. 2 is a block diagram of the components comprising one embodiment of this invention.

Referring to FIG. 2 and as discussed above, the system includes two or more input-output (I/O stations, for example, I/O stations C-1 and C-2. (See also FIGS. 3 and 4.) Each station consists of two major assemblies, one assembly which supplies the output of information to the users of the system and the other assembly which collects input information from the users.

The output assembly includes a visual display 50 which may be in the form of a plasma display or a cathode ray tube display in which text type information and/or graphical information can be displayed to the user. Additional forms of output could include an audible signal which may be used to catch the attention of the user and/or audible information in the form of speech or code.

In the embodiment of this invention illustrated in the drawings, the input assembly of each I/O station consists in part of a set of pushbuttons 53-62 (which are used by the person(s) of the medical team assigned to the station) to answer questions which are displayed on the display 50 and which are also used to control the sequencing of information which is displayed. In a typical configuration, there will be two or more I/O stations, for example, I/O stations C-1 and C-2, each of which provides information to a particular location and/or team of medical personnel who are performing medical procedures on a single patient. Each display 50 provides output information and accepts input information from a different person or team and coordinates the activities of these various individuals or teams.

As shown in FIG. 2, I/O stations C-1 and C-2 communicate with the central control unit A either by a cable or by telemetry. I/O stations C-1 and C-2 may be located remotely from control unit A or be directly connected thereto. Furthermore, each I/O station is typically located such that it is readily accessible to the specific persons who are involved in carrying out the subject medical procedures. Control unit A controls the flow of information to and from I/O stations C-1 and C-2 and to and from the other components of the system. Every signal within the system must pass through or be generated in control unit A. Control unit A is typically a digital computer such as a Model PDP-11/03 manufactured by Digital Equipment Corporation.

In some embodiments of this invention, automatic patient monitoring apparatus I such as a pulse rate monitor, blood pressure monitor, etc., could be attached to the patient undergoing treatment and its output fed directly to control unit A. In these embodiments, some of the patient's parameters would be known to control unit A without the need of the I/O station medical personnel dialogue. This would tend to speed up the treatment of the patient under some circumstances.

A sequence of instructions used to direct the operation of the control unit A is stored in program store B. These instructions are encoded in a form compatable with the instruction set of control unit A. Program store B might typically consist of a solid state memory, core memory, or read only memory.

A boot strap included in control unit A causes control unit A to begin fetching instructions from program store B. The initial sequence of instructions sent to control unit A from program store B causes control unit A to fetch encoded information from random access mass memory D and to decode this information and transmit it to designated I/O stations. Thus, random access mass memory D contains encoded information which after decoding is displayed on appropriate I/O stations. Random access mass memory D also contains control information which is used in determining the sequence in which information is displayed at the I/O stations. The information displayed on I/O stations C-1 and C-2 can be made specific to a particular medical procedure by combining the encoded information stored in random access memory D, together with the associated control sequencing information. Examples of such procedures include a treatment of cardiac arrest, the initial management of a patient with multiple gunshot wounds, and the initial management of a patient with multiple traumatic injuries. The information required for each of such procedures is stored in a different part of the random access mass memory D and can be selected in advance of the treatment.

Information contained in random access mass memory D is organized into units referred to as frames. A frame of information is defined to be all of the information which appears at one time on the outputs of the I/O stations C-1 or C-2. Alternatively, a frame may consist of the information which is conveyed to medical personnel via I/O stations C-1 and C-2 by means other than visual (for example, a frame may consist of a speech sequence designed to convey a specific unit of information).

Associated with each frame is a unique identification number and one or more control specifications. These control specifications together with information input by medical personnel via I/O stations C-1 and C-2 and/or information provided by apparatus to measure patient variables are used by the program to determine the sequencing of frames.

Random access local high speed memory E stores the identification numbers of the frames of information directed to I/O stations C-1 and C-2 in the order in which those frames are sent to the respective stations. The storage of the identification numbers of the frames in sequence as presented at each I/O station makes it possible to reverse the sequence in which the frames of information are presented at each display station. This backup feature makes it possible for users of I/O stations C-1 and C-2 to retrace their steps and/or to correct errors in data entry. One of the buttons (described in detail later) on I/O stations C-1 and C-2 is used to send a signal to control unit A which in turn accesses information contained in random access local high speed memory E to cause the preceding frame to be displayed on the I/O unit. By repeatedly pushing this button, the sequence of frames can be displayed in the reverse order from the stopping point to the beginning of the operation. Information contained in random access local high speed memory E can also be used to return the system to any previous frame, thereby providing a capability to recover from data entry errors and to recover from other disruptions such as power failures. The backup and return functions are optional features of this invention.

The system can be designed such that one I/O station (at which the chief physician is located) overrides the other I/O stations. For example, the I/O station at which the chief physician is located may have a pushbutton that will back up the entire program for all the I/O stations in the system. Preferably each I/O station has a backup pushbutton for backing up the frames at its station, and the station for the chief physician not only has such a button but also one to back up all I/O stations.

Electronic real time clock F supplies data and time of day information on a continuous basis to control unit A. This clock is independent of the internal timing system associated with control unit A. Electronic real time clock F is typically a unit such as the Model TCU 50 manufactured by Digital Pathways, Inc. This clock contains a battery backup power supply which insures that it will provide correct date and timing information even though the rest of the system is deprived of its power source.

Printer G is a conventional alphanumeric printer which may be of one of several possible types including a matrix printer, a thermal printer, an electrostatic printer, etc. A relatively silent printer such as a thermal or electrostatic printer is preferred. The printer is used to provide a permanent log of the frames displayed at each I/O station and the input information provided by the user of these stations together with the time of day at which each of these events occurred. Also, printer G could print out a constant account of the patient's parameters as received by control unit A from the patient monitoring devices.

Printer G can also be used to print billing information and inventory control information. To perform these functions, frames would be displayed at stations C-1 and C-2 which require medical personnel to verify, by depressing the appropriate pushbuttons, that specific medical procedures had been performed. By maintaining the current costs of performing each of these procedures in random access mass memory D, control unit A can direct printer G to prepare a bill which lists each procedure performed and the associated cost of each procedure. In a similar manner, the quantities of medical supplies and materials and drugs which are used during the medical procedures in conjunction with a specific patient can be accumulated by control unit A, and a report can be printed by printer G which can be used for inventory control purposes.

A typical configuration of an I/O station is shown in FIGS. 3 and 4. Display 50, which may be a plasma-type display, a cathode ray tube display, or some other type of display capable of representing alphanumeric text and/or graphical information is protected by housing 51. An input pushbutton assembly is located in housing 52 which also contains audio speaker 63. Housings 51 and 52 are usually connected together as shown in FIGS. 3 and 4.

Pushbuttons 53 through 62 are used to feed input information from the user of the system to the control unit A. Each of these buttons (the pushbutton assemblies will be later described in detail) when depressed closes a momentary contact causing a signal to be transmitted to control unit A which identifies the particular pushbutton which has been depressed. Each pushbutton assembly contains a light source which is turned on and off under control of control unit A. Only when the control unit A causes the light source of a particular pushbutton assembly to become illuminated is that pushbutton circuit available to be activated by the user. Each pushbutton 53-62 bears an identification label and additionally is color coded to identify its function to the user.

The functions of pushbuttons 53-62 will now be described in detail. Pushbutton 61 is labeled "NEXT" and when depressed, a new frame of information appears on the visual display. Pushbuttons 60 and 62 are labeled "NO" and "YES" respectively and serve to accept "NO" and "YES" responses from the user in response to questions posed by displays 50. Pushbutton 56 is labeled "BACK ONE" and when depressed, causes the immediately preceding frame to be displayed. Pushbutton 59 is labeled "SKIP", and when depressed, causes a set of frames to be skipped such as a group which represents a procedure which the medical team considers unnecessary for the operation being performed. Pushbutton 58 is labeled "MARK", and when depressed, causes the control unit to record the number of the frame which is currently being displayed. Pushbutton 55 is labeled "BACK MARK", and when depressed, causes the sequence of frames to return to the last frame which was identified by "MARK" pushbutton 58. Pushbutton 57 is labeled "CRISIS", which upon activation asks a series of questions of the activator who in turn replies by pressing either the "YES" button or the "NO" button. Through this series of questions and answers, the system is capable of identifying the crisis. Once the computer system H has identified the crisis, a new series of questions and instructions is conveyed to the appropriate I/O station or all I/O stations. Also, after identification of the nature of the crisis, questions are asked and/or information displayed that is appropriate to that particular crisis.

Pushbutton 54 is labeled "HELP", and when depressed, causes more detailed information about a particular procedure to be displayed. Pushbutton 53 is labeled "RESET", and is used to initialize the entire system to the starting point in preparation for future use.

Communication cables and power cables for the display screen 50, the pushbutton assemblies for pushbuttons 53 through 62, and the speaker 63 pass through tube 64. Tube 64 is connected to housings 51 and 52 by swivel assembly 65 and is also attached to panel 68 by a second swivel assembly 66. Swivel assemblies 65 and 66 make it possible to adjust the position of display 50 and the pushbutton systems to be convenient for view and access by users of the system. Tube 64 is also attached to a panel by support 67 to give the I/O station further stability. Panel 68 in turn is attached to railing 69 such as manufactured by Fairfield Medical Products. Railing 69 is commonly found in hospital emergency rooms. Attachment to railing 69 is made by clamps 70 or 71. Provision is made for adjusting the height of the assembly by attaching panel 68 to railing 69 using either clamps 70 or clamps 71.

Power cables and communication line cables pass through tubing 64 into enclosure 75 which houses a power supply for display 50. Enclosure 75 also contains connections for power line 76 and data communication line 78. Data communication line 78 provides bidirectional communication to computer system H as previously described. Power switch 77 is an on-off control for activating and deactivating display 50. Rubber pads 73 are adjustable via units 72 to provide appropriate spacing between panel 68 and a wall or any other structure which supports rail 69.

Display 50 may, for example, consist of a plasma display (such as a Burroughs Self-Scan Model SII 1240-200) which may contain a microcomputer to decode the incoming digital information and generate the appropriate character sequence to produce the required display. Alternatively, display 50 could consist of a cathode ray tube with appropriate character generators for generating the text information and/or vector generators for generating appropriate graphical information. Also in the alternative, display 50 could consist of any device capable of generating text and/or graphical information including various conventional printing devices.

Figure 5:
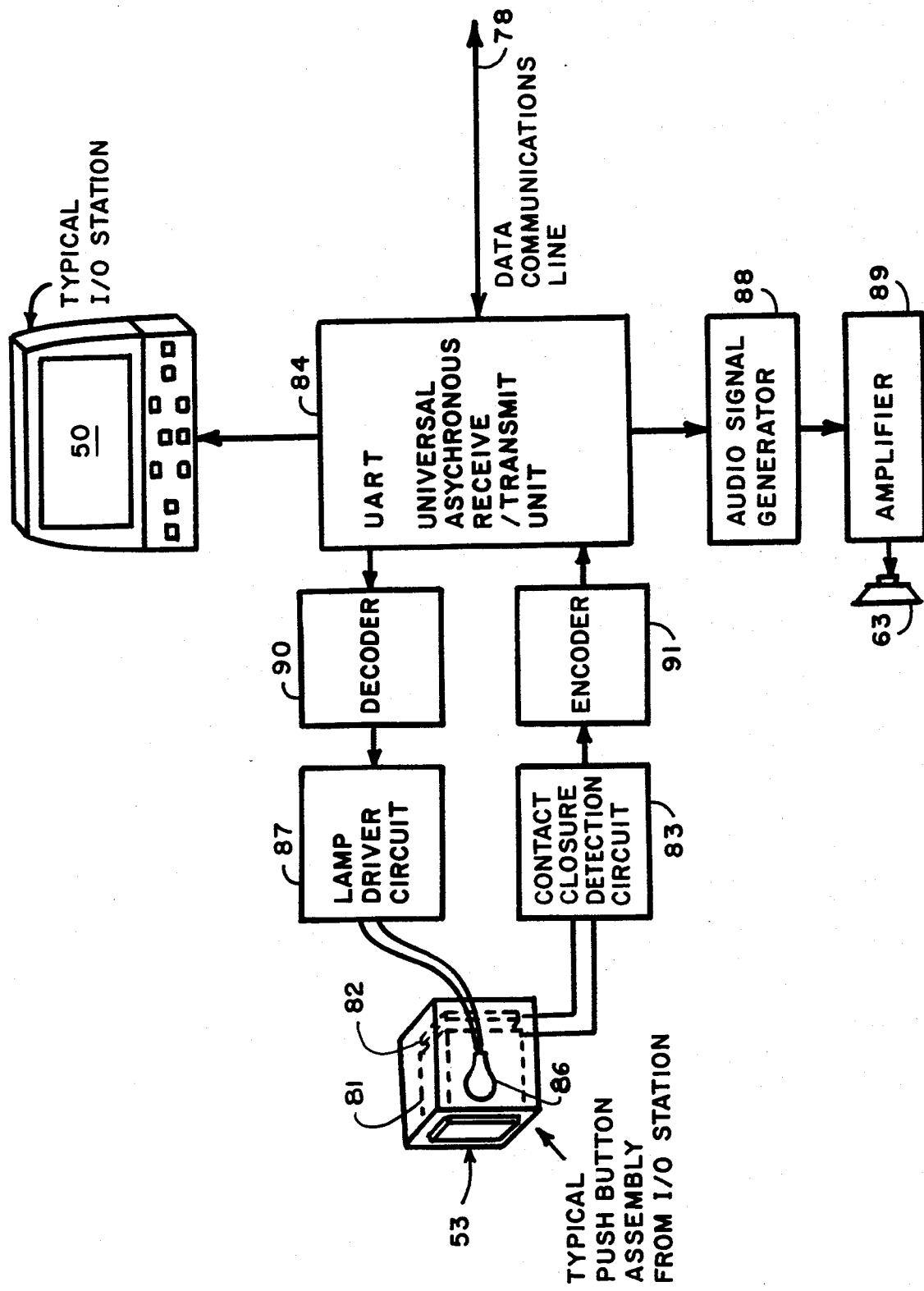
FIG. 5 is a block diagram showing a push button assembly which can be employed in the practice of this invention.

Speaker 63 can be attached internally to amplifier 89 and audio signal generator 88 (as schematically shown in FIG. 5) to produce sounds of appropriate amplitude, frequency, and duration necessary for captivating the attention of users, or alternatively, speaker 63 can be attached to appropriate amplifiers and speech synthesis systems such as the Model TM990/306 manufactured by Texas Instruments for generating intelligible speech.

The various steps and means by which pushbuttons 53 to 63 and display unit 50 communicate with control unit A via data communication line 78 are illustrated in FIG. 5. Incoming signals enter the universal asynchronous receiver/transmit unit (UART) 84 via data communication line 78 from control unit A and are decoded by UART 84 which then transmits the appropriate decoded information to display system 50, to the audio signal generator 88, and/or to one of the several lamp drive circuits associated with each of the pushbutton assemblies for pushbuttons 53 through 62.

In FIG. 5, the pushbutton assembly for pushbutton 53 serves as a typical pushbutton assembly to illustrate the design and operations of the entire set of pushbuttons 53 to 62. When incoming information on data communication line 78 is intended to cause a particular pushbutton assembly to be illuminated indicating that the relevant circuit can be activated, UART 84 generates a signal which is decoded by decoder 90 to determine which of the several lamp driver circuits 87 is to be activated. Decoder 90 sends a signal to the appropriate lamp driver circuit 87. The output of circuit 87 is a voltage which activates an incandescent or other type of light source 86. When light source 86 is activated, it causes the lettering on the lens cap (front face) of the pushbutton 53 to be illuminated. When pushbutton 53 is depressed by a user, it causes contact to occur between switch contact 81 and switch contact 82, thereby completing a circuit which causes the contact closure detection circuit to emit a pulse of predetermined amplitude and duration. This pulse is encoded by encoder 91 to identify which of the several pushbuttons has been depressed. The encoded information when received by UART 84 causes the generation of a sequence of information transmitted via data communication line 78 to control unit A which identifies which button has been momentarily depressed.

Information entering UART 84 which is destined for the generation of audible information is decoded and transmitted from UART 84 to the audio signal generator 88. Audio signal generator 88 can consist of a simple oscillator that produces a tone of specified frequency, or alternatively, it consists of a speech synthesis circuit designed to generate intelligible speech. The signal produced by audio signal generator 88 is sent to an audio amplifier 89 which in turn drives speaker 63 to produce audible sound.

UART 84 is a standard large scale integrated circuit such as is manufactured by National Semiconductor Model MM-5304. Audio signal generator 88, when serving as a tone generator, can consist of Model No. NE556, large scale integrated chip as manufactured by NEC, Inc. Alternatively, for speech synthesis, the audio signal generator could consist of a Texas Instruments Speech Synthesis Unit Model TM990/306.

The program which controls the flow of information into and out of Control Unit A is transferred from random access mass memory into random access local memory as part of the initialization process which occurs when power is applied to the system. The flow charts shown in FIG. 6 and FIG. 7 indicate the sequence of actions taken by the program in communicating with Control (I/O) Stations C-1 and C-2.

Information which can be displayed at Control Stations C-1 and C-2 is contained in a data base partitioned into units called frames which are stored in random access mass memory. Each frame contains three components: a unique identification number, text comprised of a sufficiently small number of characters to fit on the display screens of Control Stations C-1 and C-2, and control information used by the program to establish the sequence in which frames are displayed. Optionally, graphical information can be displayed on the screens of Control Stations C-1 and C-2.

Frames are grouped into sets called procedures which in most cases correspond to specific medical procedures. Each procedure is logically equivalent to a binary tree structure. One frame in each procedure is designated as the root frame and represents the starting point for the display of a sequence of frames defined by a path which traverses the tree structure.

Figure 7:
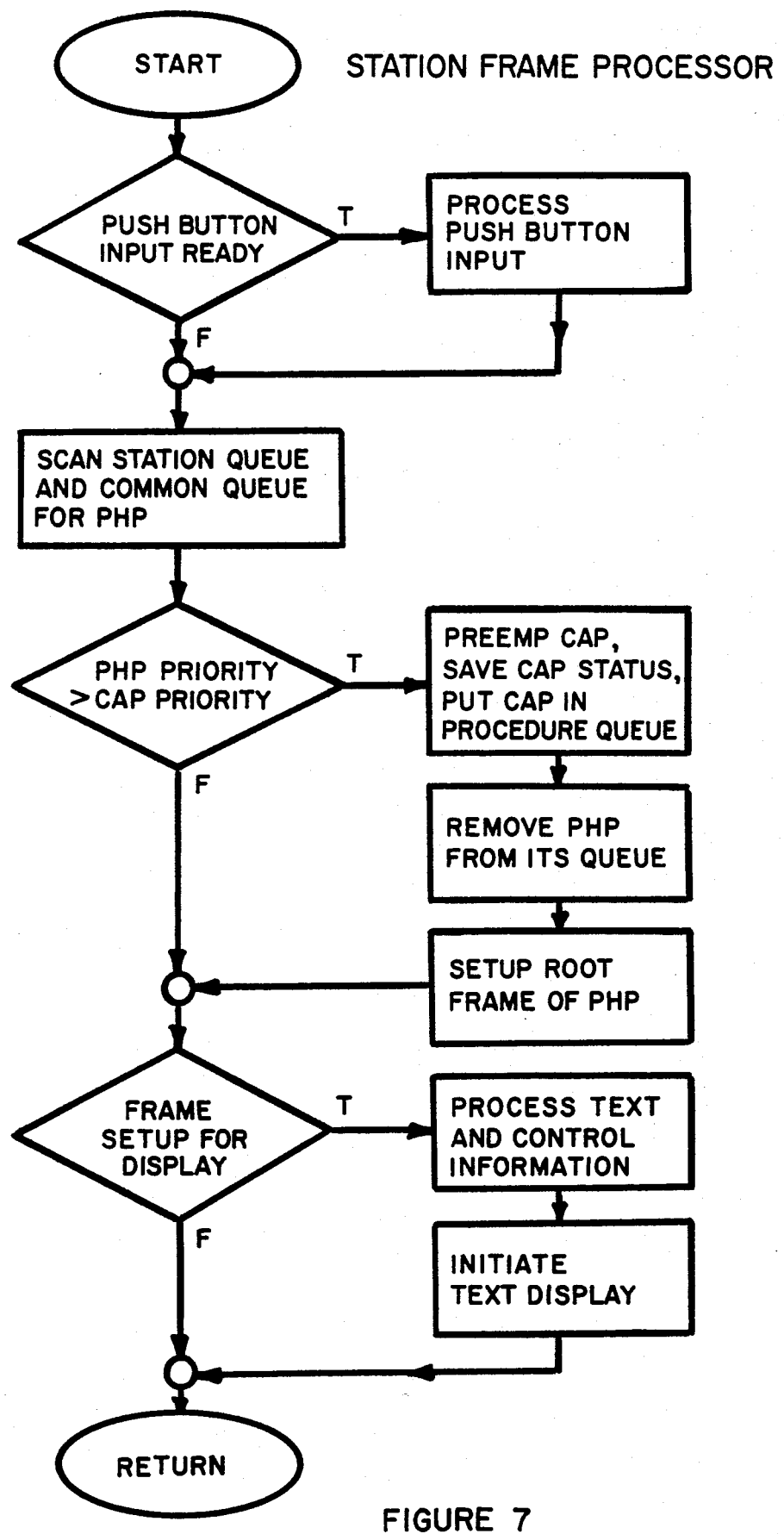
FIG. 7 is a flow chart showing the steps taken by the control program in selecting the next frame to be displayed at an I/O station.

For each I/O station, the control program maintains a queue of procedures designated as a station queue in FIG. 7. Procedures are identified by inclusion of the root frame identification number in the queue. Control information associated with each frame can include specifications that cause addition of a procedure to any designated station queue, and the assignment of a priority to the procedure. Procedures are sequenced in the station queues by priority; procedures having the same priority are sequenced by the order in which they are added to the queue. Additionally, frame control specifications can cause the deletion of a procedure from a queue or change the priority of a procedure which previously has been queued. The specified control action is taken immediately upon display of the frame which contains the control specifications.

In addition to the station queues, one of which is maintained for each I/O station, there is one common queue which contains a list of procedures appropriate for personnel to perform who are located at any I/O station. The purpose of the common queue is to balance the work load among personnel working at different control stations to compensate for different rates at which teams perform their tasks. As in the case of station queues, frame control specifications can cause procedures to be added to or deleted from the common queue and can change the priority of procedures in the common queue.

A third category of queue is designated as the timed procedure queue. Procedures in this queue are scheduled to be transferred either to a designated station queue or to the common queue at some specified time. These timed procedures are added to the timed procedure queue or deleted from the queue in accord with frame control specifications. When the time occurs for which a timed procedure is scheduled to be transferred, the procedure is deleted from the timed procedure queue and added to either the designated station queue or the common queue. For example, a procedure contained in the timed procedure queue might consist of a sequence of frames which instructs one of the medical teams to take a blood sample from the patient for laboratory analysis. One frame in this sequence might contain control information which upon display of the frame text would cause the procedure to be added to the timed procedure queue and assigned a high priority. This would cause display of the frame sequence comprising the procedure to be repeated at time intervals as indicated in the frame control specifications.

Figure 6:
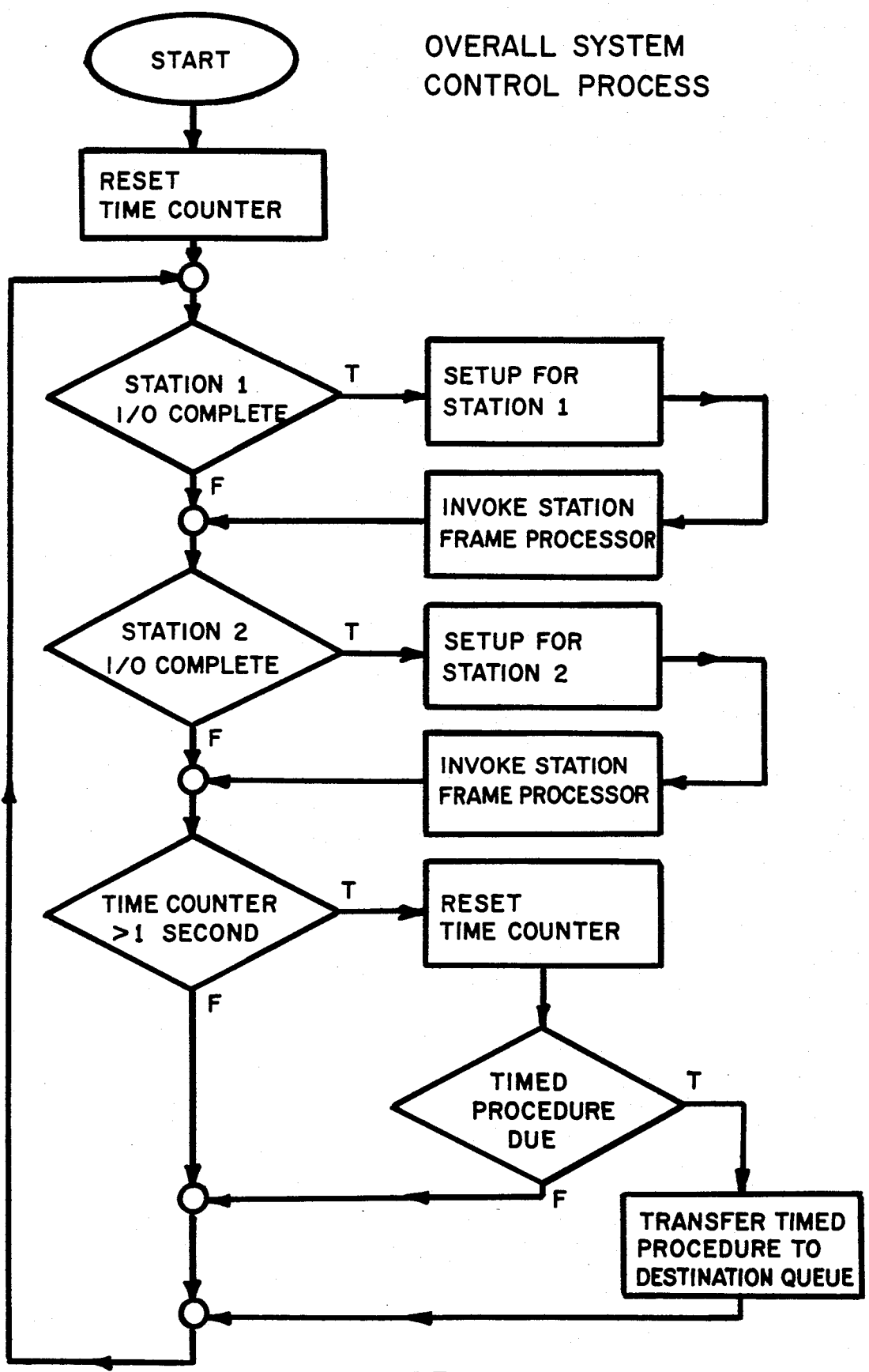
FIG. 6 is a flow chart showing the repetitive cycle of steps executed by the control program.

FIG. 6 shows a flow chart of the overall system control process. After resetting a time counter, the program enters a continuous loop. During each pass through the loop, Control Stations C-1 and C-2 are polled to determine if any input or output operation is currently being performed at that station. After verifying that I/O operations for a station are complete, a sequence of operations is performed which prepares the control unit for communication with a station. This is indicated in FIG. 6 by the flow chart elements labeled Setup For Station 1 and Setup for Station 2. The program then invokes a logic sequence called the Station Frame Processor, a flow chart of which is shown in FIG. 7.

The first step shown in FIG. 7 consists of checking to determine if input resulting from a user having depressed one of the illuminated pushbuttons at the control station is pending. If such input is pending, then the pushbutton input is processed. For example, suppose the pushbutton labeled NEXT has been depressed, the program would then examine the frame control specifications for the frame currently being displayed to determine the identification number of the frame to be displayed in response to depression of the button labeled NEXT. This frame would then be set up for display. Likewise, if the buttons labeled YES or NO had been depressed, other frames appropriate to these user responses would be set up for display as indicated in the frame control specifications.

The frame currently being displayed belongs to a procedure which is designated the currently active procedure (CAP). The CAP will terminate when a sequence of frames has been displayed which traverses the binary tree structure for that procedure.

Alternatively, the CAP may be preempted by a procedure of higher priority. The next program step shown in FIG. 7 consists of a scan of both the station queue and the common queue to locate the procedure of highest priority (PHP) in these queues. The PHP priority is then compared with the CAP priority. If the PHP priority is higher, the CAP is preempted, its status is saved and it is returned to it queue. The PHP is then removed from its queue and the root frame of the PHP is set up for display.

Next, a check is made to determine whether a frame has been set up for display. If the CAP priority is greater than the PHP priority, this frame will be part of the CAP sequence; otherwise it will be the root frame of the PHP. Once the root frame of the PHP has been set up, the PHP replaces the CAP and for purposes of further processing, the PHP is designated at the CAP. If a frame has been set up for display, the text and control information associated with the frame is processed and display of the text is initiated. Examples of control information processing might include addition of a procedure to any procedure queue, deletion of a queued procedure or alteration of the priority or time attributes of a queued procedure.

Completion of the steps defined in the Station Frame Processor flow chart of FIG. 7 results in a return to the flow chart shown in FIG. 6. Although FIG. 6 shows the logic for polling two control stations, the program is not limited to two stations but can accommodate whatever number of stations may be required for the specific application of the invention.

A time counter is next referenced to determine if at least one second has elapsed since the counter was last reset. If so, the counter is reset, and the timed procedure queue is scanned to determine if any procedure in the queue is due for transfer. If so, any such procedure is transferred to its destination queue which will be either a designated station queue or the common queue.

The steps described above complete one pass through the loop of FIG. 6. The looping process continues until the entire program is reset to START.

Other program logic capabilities not shown in the flow charts of FIGS. 6 and 7 are considered to be within the scope of this invention. These include counters which can be incremented or decremented in accord with frame control specifications and which can cause addition or deletion of procedures from any of the procedure queues conditional on the numerical value of the counters. For example, one counter might be used to represent the cumulative dosage of a particular drug administered to a patient and another counter might be used to count the number of times that a particular medical procedure such as defibrillation has been administered to a patient. Other capabilities not shown in the flow charts which are within the scope of this invention include the ability of the program to accept information from sources other than the control station pushbuttons such as from electrocardiogram analyzers and blood gas analyzers and to queue and dequeue procedures in accord with such information.

ILLUSTRATIVE EXAMPLE AND SAMPLE FORMS

Below is a subset of frames which illustrate the way in which this invention coordinates the efforts of a cardiac arrest resuscitation team. The team consists of two physicians designated as Doctor A and Doctor B, and three nurses designated as Nurse A, Nurse B and Nurse C. Each frame contains a unique identification number in the upper right hand corner which is used in the following discussion to identify specific frames in the subset:

```
DOCTOR A:                          7100
YOU AND NURSE B CONTINUE CPR
DOCTOR A:
HAVE NURSE A GIVE ATROPINE SULFATE
(& 07 MG IV PUSH)
AFTER 1 MINUTE IS THE VENTRICULAR
HEART RATE STILL LESS THAN 60/MIN?
```

```
DOCTOR A:                          7101
DOES THE EKG SHOW
ELECTROMECHANICAL DISSOCIATION
OR ASYSTOLE?
```

```
DOCTOR A:                          7103
DOES THE EKG SHOW VENTRICULAR
FIBRILLATION?
```

```
DOCTOR A:                          7104
1. YOU AND NURSE B CONTINUE CPR
2. HAVE NURSE A GIVE ATROPINE
   SULFATE (& 07 MG IV PUSH)
3. HAVE DOCTOR B PREPARE FOR
   PACEMAKER INSERTION
AFTER 1 MINUTE IS THE VENTRICULAR
HEART RATE STILL LESS THAN 60/MIN?
```

```
DOCTOR A:                          7105
DOES THE EKG SHOW
ELECTROMECHANICAL DISSOCIATION
OR ASYSTOLE?
```

```
DOCTOR A:                          7106
DOES THE EKG SHOW VENTRICULAR
FIBRILLATION?
```

```
DOCTOR A:                          7107
1. YOU AND NURSE B CONTINUE CPR
2. HAVE NURSE A GIVE ATROPINE
   SULFATE (& 07 MG IV PUSH)
AFTER 1 MINUTE IS THE VENTRICULAR
HEART RATE STILL LESS THAN 60/MIN?
```

```
DOCTOR A:                          7108
DOES THE EKG SHOW
ELECTROMECHANICAL DISSOCATION
OR ASYSTOLE?
```

```
DOCTOR A:                          7109
DOES THE EKG SHOW VENTRICULAR
FIBRILLATION?
```

```
DOCTOR A:                          7110
1. YOU AND NURSE B CONTINUE CPR
2. HAVE NURSE A GIVE ATROPINE
   SULFATE (& 07 MG IV PUSH)
AFTER 1 MINUTE IS THE VENTRICULAR
HEART RATE STILL LESS THAN 60/MIN?
```

```
DOCTOR A:
DOES THE EKG SHOW
ELECTROMECHANICAL DISSOCIATION
OR ASYSTOLE?
```

```
DOCTOR A:                          7112
DOES THE EKG SHOW VENTRICULAR
FIBRILLATION?
```

-continued

| | |
|---|---|
| DOCTOR A: 7113<br>1. HAVE NURSE A:<br>  START ISOPROTERENOL DRIP<br>  (& 10 MG IN 250 ML D5W)<br>  TO RUN AT 4 MICROGRAM/MIN<br>2. HAVE DOCTOR B:<br>  PREPARE TO INSERT PACEMAKER<br>  WIRE THROUGH EITHER SUBCLAVIAN<br>  ROUTE (LEFT SIDE PREFERABLE)<br>AFTER 1 MINUTE, DOES EKG SHOW<br>ELECTROMECHANICAL DISSOCIATION OR<br>ASYSTOLE? | DOCTOR B: 8000<br>ARE TWO CENTRAL VENOUS CATHETERS<br>IN PLACE? |
| DOCTOR A: 7115<br>DOES THE EKG SHOW VENTRICULAR<br>FIBRILLATION? | DOCTOR B: 8020<br>IS A SUBCLAVIAN CATHETER ALREADY<br>IN PLACE? |
| DOCTOR A: 7117<br>HAS THE VENTRICULAR HEART RATE<br>INCREASED TO GREATER THAN 60/MIN? | DOCTOR B: 8001<br>USING THE CORDIS CATHETER ASSEMBLY<br>INSERT GUIDE WIRE THROUGH THE<br>& 76 GAUGE CATHETER<br>DOES THE GUIDE WIRE PASS THROUGH<br>THE CATHETER EASILY? |
| DOCTOR A: 7118<br>HAVE NURSE A INCREASE<br>ISOPROTERENOL DRIP TO & 48<br>MICROGRAMS/MIN<br>AFTER 1 MINUTE DOES THE EKG SHOW<br>ELECTROMECHANICAL DISSOCIATION<br>OR ASYSTOLE? | DOCTOR B: 8002<br>1. PUSH THE GUIDE WIRE THROUGH THE<br>  CATHETER UNTIL JUST THE TIP<br>  PROTRUDES AND BY GRASPING BOTH<br>  CATHETER AND GUIDE WIRE PULL<br>  CATHETER SLOWLY UNTIL GUIDE<br>  WIRE AT CATHETER TIP IS SEEN<br>  THEN GRASP GUIDE WIRE AS IT<br>  ENTERS SKIN<br>2. REMOVE CATHETER BY SLIDING<br>  OVER GUIDE WIRE |
| DOCTOR A: 7121<br>DOES THE EKG SHOW VENTRICULAR<br>FIBRILLATION? | DOCTOR B: 8003<br>3. MAKE A SMALL (5 MM) INCISION<br>  IN SKIN WHERE GUIDE WIRE<br>  PASSES THROUGH<br>4. PASS CORDIS ASSEMBLY CATHETERS<br>  (BLUE AND WHITE) OVER GUIDE<br>  WIRE UNTIL TIP OF GUIDE WIRE<br>  PROTRUDES FROM WHITE HUB<br>5. HOLDING TIP OF GUIDE WIRE<br>  FIRMLY, PASS BOTH COROIS<br>  ASSEMBLY CATHETERS (BLUE AND<br>  WHITE) OVER GUIDE WIRE INTO<br>  SUBCLAVIAN VEIN |
| DOCTOR A: 7125<br>IS THE VENTRICULAR HEART RATE<br>GREATER THAN 60/MINUTE? | DOCTOR B: 8018<br>6. REMOVE GUIDE WIRE AND BLUE<br>  INNER CATHETER<br>7. SUTURE WHITE CATHETER HUB TO<br>  SKIN |
| DOCTOR A: 7127<br>IS THE VENTRICULAR HEART RATE<br>GREATER THAN 100/MINUTE? | DOCTOR B: 8004<br>1. HAVE NURSE C ATTACH IV TO IV<br>  TUBING ASSEMBLY ON WHITE CORDIS<br>  CATHETER AND INFUSE APPROPRIATE<br>  FLUID<br>2. THREAD THROUGH THE WHITE<br>  CATHETER THE PACEMAKER WIRE<br>  WITH THE NATURAL CURVE DIRECTED<br>  CAUDALLY<br>3. ATTACH TO THE PACEMAKER WIRE<br>  WITH A PINCH CLAMP THE V LEAD<br>  FROM THE EKG MACHINE AND SLOWLY<br>  ADVANCE THE CATHETER INTO THE<br>  HEART WHILE WATCHING THE EKG<br>  TRACING |

```
DOCTOR A:                        7128
DOES THE EKG SHOW VENTRICULAR
TACHYCARDIA?
```

```
DOCTOR B:                        8005
1. HAVE NURSE C PREPARE PACE
   GENERATOR BY CHECKING POWER
   AND BATTERIES
2. HAVE HER SET MA TO & 68
3. HAVE HER SET RATE TO & 37
4. HAVE HER SET SENSITIVITY TO
   & 39
DOES THE V LEAD SHOW VENTRICULAR
ECTOPIC BEATS?
```

```
DOCTOR B:                        8008
1. ATTACH PACEMAKER WIRE TO PACE
   GENERATOR
2. BY WATCHING EKG TRACING CONFIRM
   PROPER PLACEMENT OF PACEMAKER
   WIRE AND PROPER PACING
IS THE PACE ARTIFACT PRESENT ON
THE EKG STRIP?
```

```
DOCTOR B:                        8010
IS THE PACEMAKER PACING THE HEART
AT THE DESIRED RATE?
```

```
DOCTOR B:                        8012
1. SUTURE PACEMAKER WIRE IN PLACE
2. REDUCE MA UNTIL THE GENERATOR
   JUST CAPTURES THE VENTRICULAR
   HEART RATE
```

Frames 7100 through 7112 appear on one of the two display screens designated for use by the physician in charge of the resuscitation effort. The information on each of these frames contains a question which requires either a "YES" or "NO" response. The response is indicated by depressing an appropriate pushbutton labeled "YES" or "NO". The sequence of frames which is displayed will depend on the specific responses given. In this sequence, Doctor A is treating a bradycardia condition with the assistance of Nurse A and Nurse B.

At Frame 7113, it has been determined that the patient requires a pacemaker. This pacemaker is to be inserted by Doctor B while Doctor A continues the resuscitation treatment. As indicated in the example, when Frame 7113 appears on the display screen for Doctor A, the system simultaneously displays Frame 8000 on a second screen for Doctor B. As Doctor A continues the resuscitation as indicated by the sequence of Frames 7113 through 7128, Doctor B is inserting a pacemaker with the help of Nurse C in accord with the sequence of Frames 8000 through 8012. Doctor A and Doctor B can proceed through the sequence of frames designated for each of them at whatever pace is appropriate. However, should a procedure of higher priority be required as indicated by responses given by Doctors A or B, the procedure being followed by Doctors A and/or B would be temporarily interrupted and a new sequence of frames would be displayed.

In Frames 7100, 7104, 7107, 7110, 7113, 7118, 8001, and 8005, there are references to drug dosages or catheter sizes which are dependent on information such as the weight of the patient. In actual use, the symbol "&" and the two digit number which follows in the above listed frames are replaced by specific drug dosages or catheter sizes appropriate to the patient as computed by the system.

Once given the above disclosure, other features, modifications, and improvements will become apparent to one skilled in the art. Such features, modifications, and improvements are, therefore, considered to be within the scope of this invention as defined by the following claims.

We claim to have invented:

1. A system for coordinating the actions of at least two persons upon a common patient comprising:
   at least two input-output stations, located in proximity to each other, one for use by a first one of said persons and one for use by a second of said persons, each of said stations having (a) input means permitting the person complementary to that station to enter medical data and (b) output means for communicating information to the person complementary to that station, and
   control means responsive to the medical data from each said input means for giving coordinated different instructions to said first and second persons based on said data via said output means that are respectively complementary to the first and second persons,
   whereby the instructions given by the plural output means for treatment of the patient by said persons are in a coordinated and desired sequence that depends on the data on the patient that is fed into the system.

2. A system as defined in claim 1 in which said control means includes selecting and sequencing means for controlling the supply of output information to said stations including the selection of desired output information for the stations whereby to provide the emission of output information in a desired sequence that depends at least in part on the input data fed into said stations.

3. A system as defined in claim 1, wherein each said station has a single unit upon which its said input means and its said output means are mounted and in which the input means comprises pushbuttons.

4. A system as defined in claim 1 in which each said input means includes at least one pushbutton and in which at least one said pushbutton at each station has illuminating means to illuminate the same, said control means including means to ask a question via one of said output means and controlling the illuminating means to illuminate a pushbutton when it is one that the person who is asked the question may wish to depress in order to answer the question.

5. A system as defined in claim 1 in which said input means comprises
   at least several pushbuttons,
   designating means associated with said pushbuttons to indicate a plurality of said pushbuttons, each of which when depressed will provide a possible answer to a question posed by said output means, and
   said control means including means for delivering a question to one of said output means and operating the designating means to indicate the plural pushbuttons which may be depressed to answer the question.

6. A system as defined in claim 1 in which at least one of said stations has indicating means associated with its said input means,
   said control means including means for transmitting a question to the output means of said last-named station and for operating said indicating means in a manner which will assist the person associated with said last-named station to operate the input means at said last-named station to enter the answer to such question via the input means of said last-named station.

7. A system as defined in claim 1 in which at least one of said output means has a visual display for displaying said output information.

8. A system as defined in claim 1 in which at least one of said output means produces an audible output of information.

9. A system as defined in claim 1 in which at least one of said output means has both visual and audible outputs.

10. A system as defined in claim 1 in which at least one of said output means has both visual and audible outputs of the same information.

11. A system as defined in claim 1 in which at least one station has an output means comprising a visual display and input means comprising pushbuttons for entering input data.

12. A system as defined in claim 1 in which at least one station has an output means comprising an audible output device and input means comprising pushbuttons.

13. A system as defined in claim 1 which is associated with a patient's bed,
    said stations being located at different positions adjacent said bed so that each of said persons is associated with only one of said stations and each such said person co-acts only with his complementary said station.

14. A system as defined in claim 1 in which said control means supplies information to the plural output means in a multiplicity of frames which occur in series and with at least some frames including output information to each output means to be communicated to said complementary person, the output information to each output means in each said frame including either a question or an instruction,
    said control means also including means requiring at least one input means to receive input information after each question or instruction before the control means advances the output information to the next frame.

15. A system as defined in claim 14 in which at one station the input means includes a backup input,
    said control means including means responsive to operation of the backup input to change the output at the last-named station to an output corresponding to that for the immediately preceding frame.

16. A system as defined in claim 14 in which at one station the input means includes a backup input,
    said control means including means responsive to operation of the backup input to change the outputs at all of the stations to outputs corresponding to those for a preceding frame.

17. A system as defined in claim 14 in which at one station the input means includes first and second backup inputs,
    said control means including means (a) responsive to the first backup input to change the outputs at all of the stations to outputs corresponding to those for a preceding frame, and (b) responsive to the second backup input to change the output at said one station to an output corresponding to that for the immediately preceding frame for that said station.

18. A system as defined in claim 14 including timing means for providing time signals enabling the time of occurrence of each frame and of each entry of input information to be determined.

19. A system as defined in claim 14 including recording means for recording (a) the output information produced during each frame and (b) the input information fed into the system via the input means.

20. A system as defined in claim 19 wherein said recording means receives said timing signals and records the time of occurrence of said frames and of entries of input information into the system via said input means.

21. A system as defined in claim 14 including memory means storing the prices of a multiplicity of acts or substances, and
    recording means for recording the prices of acts performed or substances administered during operation of the system.

22. A system as defined in claim 21 in which the control means totalizes the prices of the acts or substances administered and the recording means records such total.

23. A system as defined in claim 1 further comprising measuring means associated with the patient to measure at least one of the patient's operating parameters, said control means including means for receiving the output of said measuring means and using the received data in subsequent instructions to at least one of said output means.

24. A system as defined by claim 1 in which the control means and the input-output stations assume at least some of the duties normally performed by the chief of a team of medical personnel in directing the treatment of the patient.

25. A method of utilizing at least two input-output stations and a control unit for coordinating the actions, upon a common patient, of a medical team comprising
    providing at least one person of said medical team one of said input-output stations and providing at least one other person of said medical team another one of said input-output stations, storing a multiplicity of frames of output information in said control unit with each said frame having output information for at least one of said stations, a person of said team at each of the plural stations supplying input information to the station responsive to output information at the station, advancing the output information at the stations to a new frame in response to receipt of input information, said medical team answering questions about the patient propounded by the output information by entering input information responsive to the question into the station whose output propounded the question, and the personnel of said medical team coordinating their treatment of the patient in a sequence directed by the output information, whereby the selection and sequence of at least some of the frames depends at least in part upon the said answers to questions and also upon the prior treatment of the patient as called for by the output information.

26. The method of claim 25 in which said selection and sequence is in accordance with a predetermined program which provides for varying the selection and sequence depending upon the patient's condition as indicated at least in part by said input information.

27. The method of claim 25 in which the output information in one frame at one station is reset to an item of output information in an earlier frame.

28. The method of claim 25 in which the output information in one frame at all stations is reset to the output information in an earlier frame.

29. The method of claim 25, 26, 27, or 28 in which the time of occurrence of each event is recorded.

* * * * *